United States Patent [19]

Roiret et al.

[11] 4,225,245
[45] Sep. 30, 1980

[54] APPARATUS FOR MEASURING THE OPTICAL TRANSMISSIVE POWER OF THE ATMOSPHERE

[75] Inventors: Michel Roiret, Massy; Aimé Salles, Courbevoie; Michel Dupitier, Le Port Marly, all of France

[73] Assignee: Societe Nationale d'Etude et de Construction de Moteurs d'Aviation (S.N.E.C.M.A.), Paris, France

[21] Appl. No.: 909,953

[22] Filed: May 26, 1978

[30] Foreign Application Priority Data

May 31, 1977 [FR] France .............................. 77 17173

[51] Int. Cl.² .......................................... G01N 21/22
[52] U.S. Cl. ..................................... 356/437; 250/205
[58] Field of Search ............................. 356/432–435, 356/437–442, 414; 250/205

[56] References Cited

U.S. PATENT DOCUMENTS

| | | | |
|---|---|---|---|
| 3,329,821 | 7/1967 | Lesage | 356/435 X |
| 3,422,271 | 1/1969 | Fuhrmann | 356/411 |
| 3,670,202 | 6/1972 | Paine et al. | 250/205 |
| 3,698,820 | 10/1972 | Hanff et al. | 356/435 |
| 3,746,452 | 7/1973 | Teboul et al. | 356/435 |
| 3,838,925 | 10/1974 | Marks | 356/438 |
| 4,095,098 | 6/1978 | Looper | 356/435 X |

FOREIGN PATENT DOCUMENTS

| | | |
|---|---|---|
| 2111483 | 5/1972 | France . |
| 2126017 | 9/1972 | France . |
| 2130819 | 10/1972 | France . |
| 2226070 | 11/1974 | France . |

*Primary Examiner*—John K. Corbin
*Assistant Examiner*—Bruce Y. Arnold
*Attorney, Agent, or Firm*—Fitzpatrick, Cella, Harper & Scinto

[57] ABSTRACT

An apparatus for measuring the optical transmissive power of the atmosphere, having particular application to measuring visibility at airports, in which luminous flux from a source passes to a remote first detector through the atmosphere, and flux from the source also passes to a second detector through a fibre optic arrangement. The output of the second detector is compared with a reference signal and the difference signal from the comparator is fed to a variable gain amplifier which controls the light source to remove errors in the output of the first detector which would otherwise occur by virtue of aging of the detectors and/or by virtue of changes in the luminosity of the source. Also described is an arrangement for compensating for accumulation of dirt on the detectors and/or the luminous flux source without cleaning off the dirt.

7 Claims, 2 Drawing Figures

APPARATUS FOR MEASURING THE OPTICAL TRANSMISSIVE POWER OF THE ATMOSPHERE

FIELD OF THE INVENTION

This invention relates to apparatus for measuring the optical transmissive power of the atmosphere, and has particular but not exclusive application to providing an indication of visibility at airports.

BACKGROUND OF THE INVENTION

For some years, investigations have been made for measuring the visibility on or near runways of an airport. The visibility depends on the transparency or transmissive power of the atmosphere hereinafter referred to, for greater convenience, as PTA.

The subject of the present invention is an apparatus enabling this PTA to be measured in a very precise and very simple manner.

Numerous devices are already known which are based on the response of a photosensitive cell receiving, through a certain path within the atmospheric medium to be studied, the light beam emitted by a source situated at the other end of the path, the said response naturally varying as a function of the transmissive power of the medium. The major difficulty in operating these installations, arises from the fact neither the intensity or luminance of the luminous source nor the sensitivity of the photosensitive cell are constant with time. Various automatic compensating arrangements have already been proposed for overcoming correlative errors. In particular, in French Patent Application No. 71.09954 of Mar. 22, 1971, now French Patent No. 2,130,819, the applicants proposed using an auxiliary light emitter irradiating the same photosensitive cell over a trajectory the absorption of which is independent of the fluctuations in the medium to be studied, the luminosities of the main and auxiliary sources being mutually controlled in such a manner that the fluxes received by the cell originating from the two emissions, are at a constant ratio. For correcting variations in the sensitivity of the cell, such a device also comprises a control arrangement between the said cell and the auxiliary source so as to maintain the light emission from the auxiliary source in inverse proportion to the sensitivity of the cell.

Technically, the above system gives every satisfaction. However, for proper operation, it requires the presence of a qualified maintenance staff. The frequent absence at small airports of specialised staff for maintaining such equipment necessarily means that the maintenance operations much be less frequent and as simple as possible at site level.

SUMMARY OF THE INVENTION

The apparatus for measuring the PTA in accordance with the invention includes an electrically driven luminous source driven by a current supply device, the source emitting a beam of luminous flux through the atmosphere to a receiving station at which a first detector provides an electric current in proportional relationship with the luminous flux received after passage through the atmosphere. Also, part of the flux emitted by the source, is transmitted directly, by means of a fibre optic light guide, to a reference second detector identical to the first detector.

According to one form of the invention, a comparator compares the second detector current with a substantially constant reference signal and delivers a difference signal which is cancelled by means of a control loop which controls the light intensity of the source, the first detector electric current thus constituting an information current proportional to the PTA.

In accordance with another form, a divider circuit produces the ratio of the measuring electric current to the reference electric current and delivers an information current proportional to the PTA.

Losses of the flux incurred in the fibre optic light guide, being a function of the spectrum of the emitted light, preferably are compensated for by the use of a filter so as to render the operation of the apparatus independent of the said spectrum. This filter may with advantage be situated in the light beam passing through the atmosphere, in which case it then has a spectral response proportional to that of the light guide. This filter may also be situated in the luminous beam passing through the fibre optic light guide; it then has a spectral response such that, combined with that of the light guide, the loss in the light guide plus that of the filter is independent of the spectrum.

So as to reduce the effects of dirt becoming deposited on the windows of the emitter and receiver, the apparatus for measuring PTA in accordance with the invention, also preferably includes a calibration device by means of which, at an instant determined by an operator, the signal from the first detector is compared with a reference standard, the difference signal thus obtained being cancelled by means of a control loop controlling the gain of a measuring amplifier connected to the first detector. In this arrangement, each reference standard has a value such that the comparison with the information current provides a zero difference signal when the information current is that of a PTA corresponding to a visibility at a predetermined distance which the operator, generally situated in the airport control tower may himself judge by means of landmarks situated within the landscape.

BRIEF DESCRIPTION OF THE DRAWINGS

In order that the invention may be more fully understood and readily carried into effect, embodiments thereof will now be described by way of illustrative example with reference to the accompaying drawings wherein.

DESCRIPTION OF PREFERRED EMBODIMENT

Figure 1:
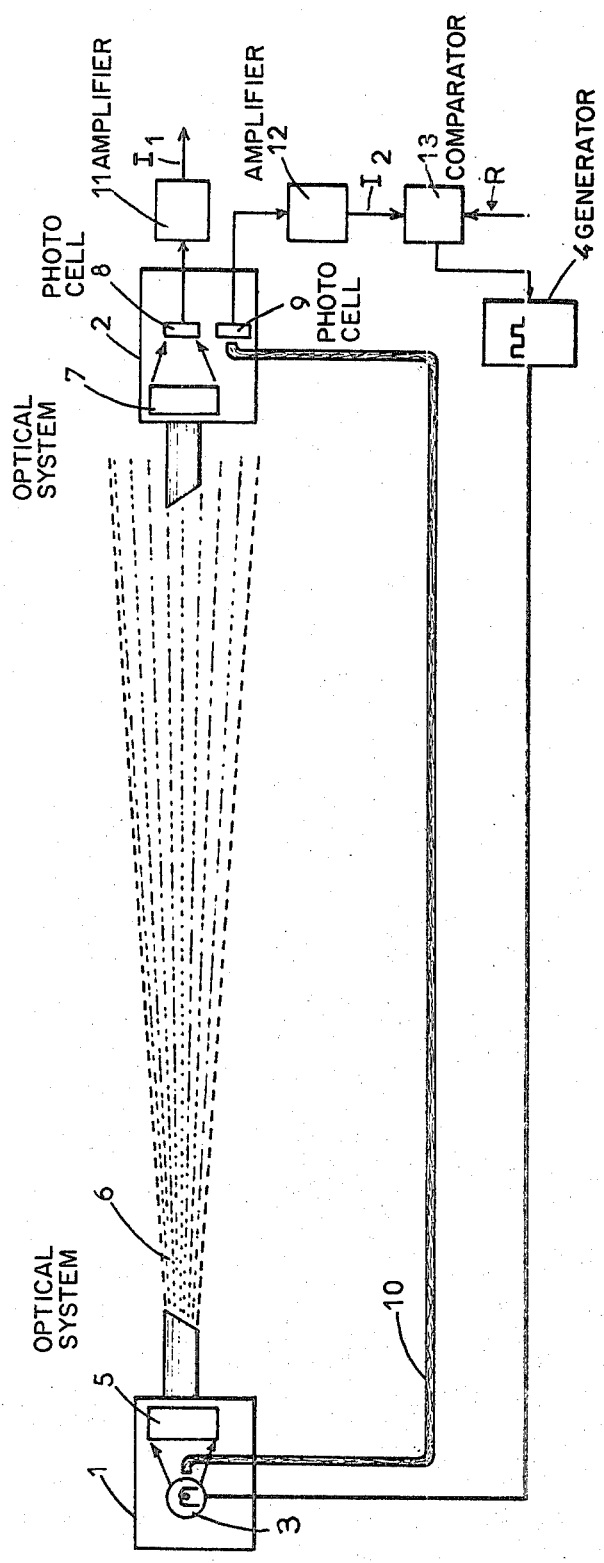
FIG. 1 is a schematic diagram of an apparatus in accordance with the first embodiment of the invention.

In known manner, the apparatus for measuring the PTA illustrated in FIG. 1 comprises a light emitter 1 and a receiver 2 situated respectively at the ends of the measuring base. The emitter 1 comprises a luminous source 3 supplied by an electric generator 4. As far as the source 3 is concerned, the choice of a monochromatic or a narrow spectrum source is only acceptable to the extent where the coefficient measured within the spectrum of the source is proportional to the coefficient of atmospheric extinction. However, the studies and results of experiments carried out within this field, show that the correlation is only satisfactory to the extent where the meteorological visibility is less than a limit between 500 and 600 meters inclusive. Furthermore, if the emission frequency of such a source can be selected so that it is located outside the absorption lines of water vapour, it is possible to foresee the nature of the pollution which may be encountered at the different sites (kerosene vapour for example). Thus, in the case where the spectrum of the source is situated within the absorption spectrum of the pollutant, the measure is more or less erroneous according to the concentration of the latter. Moreover, it is as well to note that although a monochromatic source, in particular a laser type source, enables the complexity of the projector to be considerably reduced, its life remains limited and the cost of its replacement is high. Consequently, the luminous source 3 may with advantage be selected from among the incandescent lamps all the more because the cost of such a component is low and its length of life is satisfactory.

In order to reduce errors which could arise from ambient light and from its variations, the luminous intensity of the source 3 is modulated. To this end, the supply generator 4 is a generator preferably providing a voltage of the type known as a squarewave.

An optical system 5 converts the light emitted by the source 3 into a narrow beam 6 directed towards the receiver 2 where it is in part received by an optical system 7 which concentrates the trapped light on a photosensitive measuring cell 8.

It is appreciated that in an installation such as that which has just been described, the information which can be deduced from the current delivered by the photosensitive cell 8 can be considerably erroneous due to discrepancies in the characteristics of the source 3 and of the cell 8, In fact, these components are sensitive, on the one hand, to temperature drifts and on the other hand, in time, to long term variations due to aging. For example, the temperature drift of an incandescent lamp is 0.07% per degree centigrade whilst that of a silicon cell is 0.1% per degree centigrade. If special precautions are not taken, such variations in the characteristics of the components in the apparatus would lead to erroneous results of many percent which would be inadmissible.

The applicant has appreciated that although temperature and long term variations in photosensitive cells are considerable, these variations are substantially identical from one cell to another, especially if the precaution is taken of selecting them from the same production batch. In other words, the differential variations in temperature and in time of one cell with respect to another are negligible. It is on this realisation that the invention is based.

In accordance with the invention, a photosensitive cell is used referenced 9 identical to the measuring cell 8 and receiving a portion of the light emitted by the source 3 through the agency of a fibre optic light guide 10.

The photosensitive cell 8 is followed by a demodulator amplifier assembly 11 and the photosensitive cell 9 is likewise followed by a demodulator amplifier assembly 12. The following designations apply:

$\phi_o$ is the luminous flux emitted by the source 3, $K_1\phi_o$ is the portion of the flux $\phi_o$ removed by the optical fibres 10, $K_2\phi$ is the portion of the flux $\phi_o$ emitted into the atmosphere by the optical system 5, $K_1K_3\phi_o$ is the flux transmitted by the beam of optical fibres to the cell 9 (the coefficient $K_3$ corresponding to the attenuation within the bundle of optical fibres), $K_2T\phi_o$ is the luminous flux received by the optical system 7 and transmitted to the cell 8 (T being the attenuation factor which is a function of the transparency of the atmosphere), $S_1$ is the sensitivity of the measuring cell 8, $S_2$ is the sensitivity of the reference cell 9, $G_1$ is the gain of the measuring amplifier 11 and $G_2$ is the gain of the reference amplifier 12.

A measuring current $I_1 = G_1 S_1 K_2 T\phi_o$ is available at the output from the amplifier 11 and a reference current $I_2 = G_2 S_2 K_1 K_3 \phi_o$ is available at the output from the reference amplifier 12.

In accordance with the preferred embodiment illustrated in FIG. 1, a comparator 13 ensures the comparison between the reference current $I_2$ and a reference constant R. The difference signal delivered by the comparator 13 is used to control the electric generator 4 in such a manner that the consecutive variations in intensity of the luminous source 3 are such that they act on $I_2$ in the sense of cancellation of the said difference.

Due to the fact of this control loop which provides:

$$G_2 S_2 K_1 K_3 \phi_o = R$$

there is obtained:

$$\phi_\cdot = \frac{R}{G_2 S_2 K_1 K_3}$$

from which is obtained the value of the measuring current:

$$I_1 = \frac{G_1 S_1 K_2 T R}{G_2 S_2 K_1 K_3} = KT$$

Thus it is indeed proved that the measuring current delivered by the measuring amplifier 11 is indeed an information current proportional to PTA which it is desired to measure and that it is independent of the absolute variations in the source and the cells.

However, the variations in characteristics of the source 3 as well as the variations in the light intensity, in the case represented in FIG. 1, produces variations in the spectrum of the light emitted. However, the coefficient of attenuation $K_3$ of the bundle of optical fibres is a function of the spectrum of the light transmitted. Thus, a source of error results which it may be necessary to overcome in precision apparatus by using a corrective filter. According to one particular advantageous form, a filter having a spectral response proportional to that of the light guide is located at the level of the optical system 7. Such a filter could also be situated at the level of the optical system 5 of the emitter. Instead of using a filter having a spectral response identical to that of the light guide 10 situated between the source 3 and the cell 8, a filter could be used situated between the source 3 and the cell 9 and having a spectral response such that in combination with that of the light guide 10, the diminution of the light guide plus filter assembly is independent of the spectrum of the light emitted by the source 3.

The problem of dirt on the windows is inherent in apparatus for measuring PTA. Although, due to the very principle of measuring, it is unfortunately impossible to totally overcome this effect, it is nevertheless possible to reduce its effects. One classic method consists in using visors as protection against rain which constitutes the major carrier of dirt. The geometry of such visors must be especially well studied.

However, it has been found that these measures are insufficient. In fact, on such apparatus, a variation of the order of 1% per month has been noted due to dirt. If it is considered that a variation of more than 0.5% is not admissible, that means that it is necessary to carry out at least one cleaning operation of the windows every 15 days. This represents an inadmissible burden. This is why the measuring apparatus in accordance with the invention comprises a calibrating device enabling the cleaning operations to be separated by many months.

The device which will be described hereafter with regard to FIG. 2, enables the calibration method to be conveniently carried out.

Figure 2:
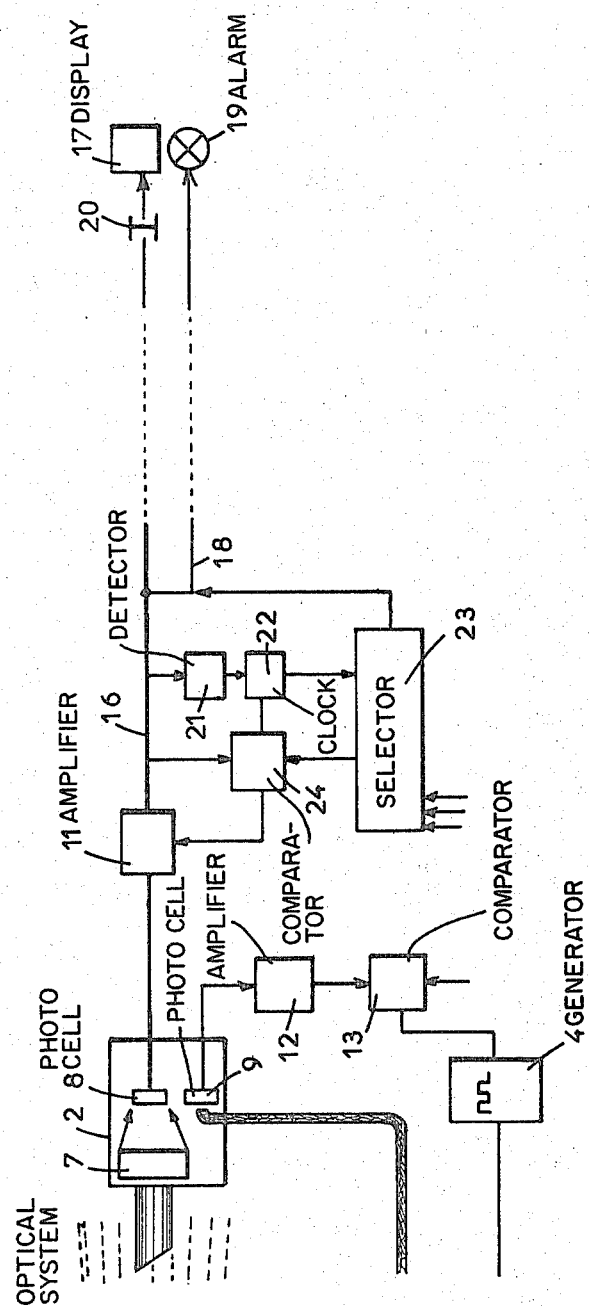
FIG. 2 illustrates the principle of the calibration system designed to reduce the disadvantages consequent upon soiling of the windows.

In FIG. 2, there are simply represented the elements which comprise the receiving portion of the assembly in FIG. 1. These elements have the same references as in FIG. 1.

In a classic manner, the measuring information delivered by the measuring amplifier 11 is transmitted through a line 16 to a display apparatus 17 located near the operator. Similarly, a line 18 supplies an alarm device 19 constituted for example by a signalling lamp which is extinguished in the case of failure of the apparatus. The lines 16 and 18 are two wires but for the sake of convenience they have been shown as single wires.

A switch 20 enabling the circuit of the line 16 to be interrupted is disposed in the circuit of the line 16 near to the operator.

At the level of the receiver, a circuit 21 ensures detection of a break in the line 16 and then starts a clock 22. This clock 22 delivers pulses to a selector 23 which selects a standard information, from among many standards, for example three, and transmits it to a comparator 24 which provides a comparison between it and the measuring information.

The difference signal delivered by the comparator 24 controls the gain $G_1$ of the measuring amplifier 11 so as to cause the measuring information to vary in such a sense that the said difference is cancelled.

Moreover, at each progression consequent upon a pulse from the clock 22, the selector 23 delivers into the line 18 a signal which controls the alarm 19 thus permitting the operator to know the position of the selector and, consequently, the standard information effectively taken into account by the apparatus. In the case of an alarm 19 constituted by a signalling lamp, the latter is extinguished at the moment when the line 16 is broken and is illuminated for an instant at each progression of the selector 23.

The different forms of standard information which can be selected for comparison in the comparator 24 with the measuring information, each have a value such that the comparison with the measuring information provides a zero difference signal when the said measuring information is exactly that of the PTA corresponding to a visibility at a predetermined distance. For example, the standard information values may have values such that the comparator 24 delivers a zero difference signal when the measuring information corresponds to a PTA of 98.21%, 99.10% or 99.55% on the assumption that the chosen reference marks correspond to visibilities of 5 kilometers, of 10 kilometers, or of 20 kilometers.

Thus, it will be understood that when the operator is in a position to determine the threshold of visibility with accuracy, he can reset the apparatus so that is provides the PTA information corresponding to the said visibility. To this end, the operator interrupts the line 16 by means of the switch 20 and selects the standard information corresponding to the visibility at the time based on the number of times the signal lamp 19 is re-illuminated.

The different values of standard information which are capable of being compared to the measuring information within the comparator 24, and under the command of the operator, are obtained in known manner in the form of standard calibrated voltages for example by means of zener diodes.

After such a calibration operation, the gain $G_1$ of the measuring amplifier 11 is such that the measuring information will have the desired accuracy for at least 15 days.

For spacing the cleaning operations of the windows sufficiently, a range of adjustment of the order of 5% of the PTA is provided. With respect to the original adjustment, this range of adjustment is advantageously arranged from at least 1% to 4% at the most. In fact, the dirt has a tendency to reduce the luminous flux received by the measuring cell 8 and consequently it is generally necessary to correct in a sense of increasing the value indicated for the PTA.

The calibration system which has just been described not only corrects measuring errors due to dirty windows but also all long term variations of various origins.

In addition to the circuits represented in FIG. 3, it is necessary to use memory circuits of quite a classic type, enabling the value of the gain of the measuring amplifier 11 to be preserved. The latter is especially useful when the operation of cleaning the windows takes place on a day when the visibility does not permit the carrying out of a calibration operation. In that case, it is advisable to provide the measuring amplifier 11 once again with a gain identical to the intitial gain. Moreover, it is of importance, that after an interruption, for example a break in the supply current to the apparatus, the measuring amplifier 11 automatically resumes the value of the gain corresponding to the last effected calibration.

As has been established, the apparatus for measuring the PTA in accordance with the invention and which has just been described has been designed so as to simplify maintenance operations to a maximum, and to make them accessible to a non-specialised staff. Its remote control calibration system, permitting a simple dialogue with the operator, constitutes an especially interesting original feature. In effect, it enables a certain and accurate compensation for the dirt on the windows and for the long term variations in the apparatus to be carried out on the site without intervention.

The various qualities of this apparatus for measuring the PTA, that is to say, its accuracy, its simplicity of operation and maintenance, and its low cost, makes it interesting for use on airports of all kinds.

What is claimed is:

1. An apparatus for measuring optical transmissive power of the atmosphere comprising:
   (a) an electrically driven source for producing luminous flux;
   (b) a current supply device arranged to supply an electric current to drive said source,
   (c) a receiver station remote from said source and including first and second detectors for producing electrical signals indicative of luminous flux incident thereon from said source, said detectors having substantially the same operating characteristics, said first detector being arranged to receive luminous flux from said source through the atmosphere;
(d) a fibre optic light guide arranged to supply light directly from said source to said second detector;
(e) means for establishing a substantially constant reference signal;
(f) a comparator for comparing the signal produced by said second detector with the said reference signal, the comparator being arranged to produce an output signal in accordance with said comparison; and
(g) means for varying the electric current supplied by said current supply device in accordance with said output signal and in such a manner as to cancel the difference between electrical signals produced by said second detector and said reference signal.

2. Apparatus as claimed in claim 1 including a filter having a spectral response proportional to the spectral response of the light guide and situated in the path of luminous flux from said source which impinges on said first detector.

3. Apparatus as claimed in claim 1 including a filter arranged in the path of light travelling in said fiber optic guide from said source to said second detector, said filter having a spectral response so arranged to render the spectral bandwidth of the flux transmitted to the second detector independent of the spectral bandwidth of the luminous flux produced by said source.

4. Apparatus as claimed in claim 1 including variable gain amplifier means arranged to amplify the signal produced by said first detector, and means for selectively varying the gain of the amplifier means in dependence upon operating conditions of the apparatus.

5. Apparatus as claimed in claim 4 including a store adapted to store predetermined gains for said amplifier, and operator controlled means for selecting a particular one of the stored gains from the store.

6. Apparatus as claimed in claim 5 including means for automatically selecting a predetermined one of said gains in response to a cessation of operation of the apparatus.

7. Apparatus as claimed in claim 5 including a control loop for controlling the gain of the amplifier in accordance with the selected stored value.

* * * * *